(12) United States Patent
Gnagnetti

(10) Patent No.: US 9,035,090 B2
(45) Date of Patent: May 19, 2015

(54) PROCESS AND APPARATUS FOR SLURRY SEPARATION OF AROMATIC CARBOXYLIC ACID

(75) Inventor: Andrea Gnagnetti, Milan (IT)

(73) Assignee: Davy Process Technology Limited, London (GB)

( * ) Notice: Subject to any disclaimer, the term of this patent is extended or adjusted under 35 U.S.C. 154(b) by 0 days.

(21) Appl. No.: 13/580,311

(22) PCT Filed: Jan. 12, 2012

(86) PCT No.: PCT/GB2012/050060
§ 371 (c)(1),
(2), (4) Date: Oct. 2, 2012

(87) PCT Pub. No.: WO2012/107733
PCT Pub. Date: Aug. 16, 2012

(65) Prior Publication Data
US 2013/0310602 A1    Nov. 21, 2013

(30) Foreign Application Priority Data

Feb. 11, 2011    (GB) .................................. 1102476.7

(51) Int. Cl.
C07C 51/42    (2006.01)
C07C 51/43    (2006.01)
B01D 29/52    (2006.01)
C07C 51/47    (2006.01)

(52) U.S. Cl.
CPC ................ *B01D 29/52* (2013.01); *C07C 51/47* (2013.01); *C07C 51/42* (2013.01)

(58) Field of Classification Search
USPC .................................................. 562/412, 416
See application file for complete search history.

(56) References Cited

U.S. PATENT DOCUMENTS 5,503,737 A    4/1996    Luthi

FOREIGN PATENT DOCUMENTS

| CN | 201485402 U | 5/2010 | | |
|---|---|---|---|---|
| WO | 02053259 A2 | 7/2002 | | |
| WO | 2010049697 A2 | 5/2010 | | |
| WO | 2010119484 A1 | 10/2010 | | |
| WO | WO 2011-017870 | * 2/2011 | ............. | B01D 33/06 |

OTHER PUBLICATIONS

International Search Report and Written Opinion for PCT/GB2012/050060, dated Apr. 18, 2012.

* cited by examiner

*Primary Examiner* — Kamal Saeed
*Assistant Examiner* — Janet L Coppins
(74) *Attorney, Agent, or Firm* — Armstrong Teasdale LLP

(57) ABSTRACT

In a process for removing aromatic carboxylic acid from a slurry thereof in solvent, the slurry is split into sub streams and each of said sub streams is supplied to a respective rotary pressure filter such that the sub stream pass through the filters in parallel. Gas is passed through the rotary pressure filters in series in an open-loop arrangement.

7 Claims, 1 Drawing Sheet

PROCESS AND APPARATUS FOR SLURRY SEPARATION OF AROMATIC CARBOXYLIC ACID

The present invention relates to a process and apparatus for use in the production of aromatic carboxylic acids and in particular terephthalic acid or isophthalic acid. More particularly it relates to a process for the removal of aromatic carboxylic acids such as terephthalic acid or isophthalic acid from a slurry. Still more particularly, it relates to a process in which the gas consumption is reduced and/or the resultant cake of aromatic carboxylic acid has a reduced moisture content than has been achievable in prior art processes or using prior art apparatus. The term 'gas' includes vapours and relates to the gas which is used for pressurisation purposes in a solids separation section of a plant.

Typically crude terephthalic acid is produced by the oxidation of p-xylene. The oxidation is conducted using acetic acid as solvent in the presence of a catalyst. The solution is then cooled in a stepwise manner to crystallise the terephthalic acid. The terephthalic acid crystals must then be removed from the acetic acid solvent and this is commonly carried out using vacuum filters. The removed crystals are then subjected to a drying step to remove residual moisture.

The crude terephthalic acid may then be subjected to a purification process. Pressure centrifuges are conventional used as part of that process. However, rotary pressure filters may be used in place of the traditional centrifuges. Examples of the use of such filters can be found in GB patent application number 1008412.7 filed 20 May 2010.

Isophthalic acid is produced by oxidising meta-xylene over a catalyst such as a cobalt-manganese catalyst. The remainder of the process for separation and purification is similar to that described above in connection with terephthalic acid. Other aromatic carboxylic acids will also be treated in a similar manner. For ease of reference, we will discuss the prior art processes with particular reference to terephthalic acid but it will be understood that the comments apply equally to other aromatic carboxylic acids.

The use of rotary pressure filters offers various advantages over more conventional systems. For example, they are more reliable than pressure centrifuges and therefore require less maintenance giving a reduction in downtime and maintenance costs.

A further advantage obtained through the use of rotary pressure filters is that they can be operated at higher pressures than the conventional vacuum filters and pressure centrifuges. This produces a drier cake of terephthalic acid which reduces the drying duty downstream of the separation step and thereby improves the economics of the system.

Another benefit associated with the use of rotary pressure filters is that a more efficient cake washing system can be used which produces a cake having a lower impurities content than is achievable with prior art systems. In addition, these pressure filters are easier to operate than the prior art centrifuges as they rotate more slowly. A still further benefit is that they offer flexibility to the process since the pressure drop and speed of rotation can readily be adjusted to optimise product output and/or operating requirements.

In order to handle the significant throughput of terephthalic acid emanating from the commercial oxidation process, multiple rotary pressure filters will be used. These are operated in parallel such that the product stream from the oxidation reaction is separated into sub streams which are passed to a filter. Whilst commonly two filters arranged in parallel will be used, the number of filters present will depend on the plant capacity and turndown philosophy.

When the rotary pressure filter is operated, a pressure drop between the filter case and the inside of the drum is achieved by means of a gas flow. The rate of gas flow will depend on the dimensions of the filter and the operating conditions such as temperature, pressure, pressure drop, cake porosity and the desired residual moisture of the cake.

As indicated above, the term "gas" includes not only gases which may be, for example one or more of an inert gas, nitrogen, oxygen, carbon dioxide, carbon monoxide and the like but also vapours such as steam and/or process vapour and should be construed accordingly.

This prior art process is illustrated schematically in FIG. 1. A slurry of terephthalic acid in solvent is passed in line 1, through filter feed pump 2 and lines 3 and 4 to filters 5 and 6 respectively. Thus the filters are operated in parallel. Gas is fed in line 7 and via lines 8 and 9 to filters 5 and 6 respectively. Blow-back gas which is used to remove the wet cake from the filter cloths of the filters is removed from line 7 and supplied in lines 17 and 18 to the drum of filters 5 and 6 respectively.

The separated filter cake is removed from filter 5 in line 10 and that from filter 6 is removed in line 11. Mother liquor and gas are removed from filter 5 in line 12 and passed to separator 13. Mother liquor and gas are removed from filter 6 in line 14 and also passed to separator 13. The separated mother liquor is removed in line 15 and the gas in line 16. The pressure of the gas from the separator has to be the same as that in the last crystalliser. This process will generally lead to a moisture content of about 12 to about 14%.

Where process gas is used, it will be understood that the flow supplied to the rotary pressure filters represents a portion of the total gas stream which would otherwise leave the oxidation reaction section of the plant and be sent to a gas expander for energy recovery. Where steam is used, the flow supplied to the rotary pressure filters represents a portion of the total steam sent to a steam turbine for energy recovery. Thus, the more gas that is required by the filters, the less that is passed to the energy recovery device and hence the less energy which can be recovered.

In an attempt to address this problem, it is conventional to operate the gas circuit to the pressure filter as a closed loop. That is to say that the gas recovered from the separator is recycled and used as the gas feed to the filters. Although make-up gas from the plant gas will be required this will generally be a relatively small amount. Whilst this solution to the problem minimises the gas requirements for the filter system and therefore the losses from the gas stream sent for energy recovery, the closed loop system does require significant items of equipment including gas/liquid separators, vapour condensers and booster compressors which increases the capital and operating costs of the system.

It is therefore desirable to provide a system which meets the requirement of minimising gas consumption and hence maximises energy recovery but which does not suffer from the disadvantages of high equipment costs of the closed loop system currently operated.

It has now been found that if the plurality of pressure filters are operated such that the gas is passed from one filter to the next i.e. the gas flow path is in series, while the slurry is passed to the filters in parallel, the problems of the prior art arrangements can be overcome. It should be understood that in the process whilst the slurry to be filtered is fed to the filters in parallel, the gas is fed through the filters in series in an open-loop arrangement.

Thus according to the present invention there is provided a process for removing aromatic carboxylic acid from a slurry thereof in solvent comprising the steps of:

(a) splitting the slurry into sub streams and supplying each of said sub streams to a respective rotary pressure filters such that said sub stream pass through the filters in parallel; and (b) passing gas through the rotary pressure filters in series in an open-loop arrangement.

As indicated above, the term "gas" includes not only gases which may be, for example one or more of an inert gas, nitrogen, oxygen, carbon dioxide, carbon monoxide and the like but also vapours such as steam and/or process vapour and should be construed accordingly.

In one arrangement, two rotary pressure filters, i.e. a first and second filter, are used. In this arrangement, the slurry is passed in parallel to the first and second filters and the gas is passed initially to the first filter and subsequently to the second filter.

Generally, the filters will be operated at different pressure levels even if their temperatures are the same. In one arrangement, the gas fed to the process may be fed at a pressure of from about 4 to about 8 barg, more preferably of from about 5 to about 7 barg. 6 barg may also be used. The gas may be let down to about 3 to about 6 barg, more preferably about 4 to about 5 barg as it supplied to the first rotary filter. As it leaves the first pressure filter it will generally be at a pressure which is lower than that at which it was supplied. Depending on the pressure drop across the first filter, the gas may be let down to reduce it further before it is applied to the second filter. Suitable pressures for the second filter may include from about 3 to about 5 or about 4 barg.

Any suitable temperature may be used. Generally the temperature will be in the range of from about 100° C. to about 160° C.

The process of the present invention offers various advantages. As the gas flow path is through the filters in series, the gas consumption will be reduced from that required with the parallel arrangements while achieving a level of moisture in the resultant cake which is comparable to that achievable with prior art arrangements. For example, where two filters are used the gas consumption will generally be reduced by 50%.

In the alternative, the process can be operated with a gas consumption which is equivalent to that noted with the prior art parallel arrangements by increasing the gas flow rate. The benefit of this arrangement is that the resultant cake moisture will be reduced thereby minimising the drying duty downstream.

The main benefit of the arrangement of the present invention is that the requirement for the auxiliary equipment used in the closed-loop prior art arrangement is obviated which decreases the capital and operating costs.

The process of the present invention may be utilised in either or both of the crude section or purification section of a process for producing an aromatic carboxylic acids.

In one arrangement, the aromatic carboxylic acid is terephthalic acid or isophthalic acid.

According to a second aspect of the present invention there is provided apparatus for the removal of aromatic carboxylic acid from a slurry thereof in a solvent comprising:
  (a) a plurality of rotary pressure filters;
  (b) means for supplying slurry to the filters in parallel; and
  (c) means for supplying gas to the filters sequentially in series in an open-loop arrangement.

In one arrangement, the aromatic carboxylic acid is terephthalic acid or isophthalic acid.

The present invention will now be described with reference to the following drawings in which.

Figure 1:
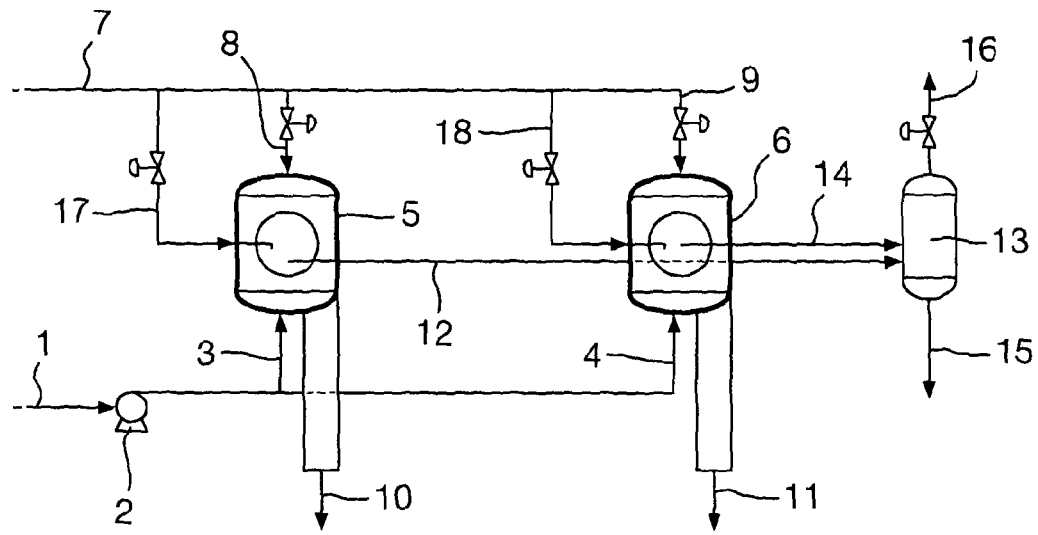
FIG. 1 is a schematic representation of the prior art.
Figure 2:
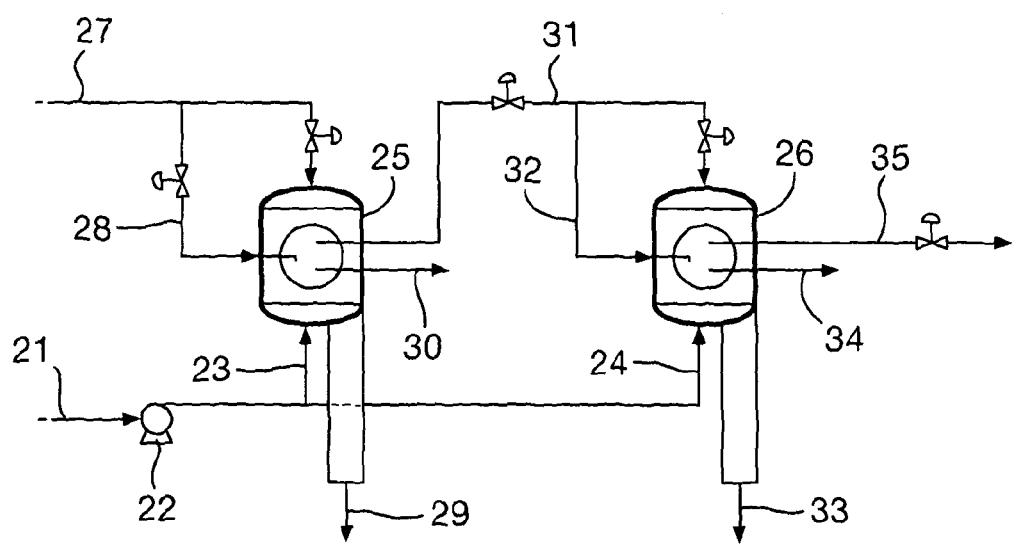
FIG. 2 is a schematic representation of the process of the present invention.

It will be understood by those skilled in the art that the drawings are diagrammatic and that further items of equipment may be required in a commercial plant. The provision of such ancillary items of equipment forms no part of the present invention and is in accordance with conventional chemical engineering practice.

For ease of reference the process will be described with reference to the separation of terephthalic acid from a slurry thereof. However, the discussions apply equally to the production of other aromatic carboxylic acids such as isophthalic acid.

A slurry of terephthalic acid in solvent is passed in line 21, through filter feed pump 22 and lines 23 and 24 to filters 25 and 26 respectively. Thus the filters are operated in parallel. The gas is passed in line 27 to the filter 25. Blow-back gas is passed in line 28 to the filter casing of filter 25. The dried filter cake is removed in line 29 and the mother liquor is removed in line 30. The gas is removed in line 31 to the filter 26. Blow-back gas is passed in line 32 to the filter casing of filter 26. The dried filter cake is removed in line 33. The mother liquor is removed from filter 26 in line 34. The gas is removed from the filter 26 in line 35.

In an arrangement where there are two filters, it is possible to operate the system of the present invention with about half the gas feed of the prior art closed loop arrangement with two filters and still achieve a filter cake from each filter having a moisture content of about 12 to about 14%. In the alternative, if a gas flow rate similar to that used in prior art closed loop system is used, a filter cake having a moisture content of about 6 to about 8% can be achieved.

The invention claimed is:

1. A process for removing aromatic carboxylic acid from a slurry thereof in solvent comprising the steps of:
  (a) splitting the slurry into sub streams and supplying each of said sub streams to a respective rotary pressure filter such that said sub streams pass through the filters in parallel; and
  (b) passing gas through the rotary pressure filters in series in an open-loop arrangement.

2. The process according to claim 1 wherein a first and second filter are present; the slurry is split into two sub streams which are passed in parallel to the first and second filters; and the gas is passed initially to the first filter and subsequently to the second filter.

3. A process for the production of crude aromatic carboxylic acid comprising the process of claim 1.

4. A process for the purification of crude aromatic carboxylic acid comprising the process of claim 1.

5. The process according to claim 1 wherein the aromatic carboxylic acid is terephthalic acid or isophthalic acid.

6. Apparatus for the removal of aromatic carboxylic acid from a slurry thereof in a solvent comprising:
  (a) a plurality of rotary pressure filters;
  (b) means for supplying slurry to the filters in parallel; and
  (c) means for supplying gas to the filters sequentially in series in an open-loop arrangement.

7. Apparatus according to claim 6 wherein the aromatic carboxylic acid is terephthalic acid or isophthalic acid.

* * * * *